(12) United States Patent
Delso et al.

(10) Patent No.: US 8,155,418 B2
(45) Date of Patent: Apr. 10, 2012

(54) AUTOMATIC GENERATION OF OPTIMAL VIEWS FOR COMPUTED TOMOGRAPHY THORACIC DIAGNOSIS

(75) Inventors: Gaspar Delso, Puteaux (FR); Antoine Collet-Billon, Paris (FR)

(73) Assignee: Koninklijke Philips Electronics N.V., Eindhoven (NL)

( * ) Notice: Subject to any disclaimer, the term of this patent is extended or adjusted under 35 U.S.C. 154(b) by 1063 days.

(21) Appl. No.: 12/065,903

(22) PCT Filed: Sep. 11, 2006

(86) PCT No.: PCT/IB2006/053214
§ 371 (c)(1),
(2), (4) Date: Mar. 6, 2008

(87) PCT Pub. No.: WO2007/031936
PCT Pub. Date: Mar. 22, 2007

(65) Prior Publication Data
US 2008/0247623 A1    Oct. 9, 2008

(30) Foreign Application Priority Data
Sep. 13, 2005 (EP) .................... 05300745

(51) Int. Cl.
*G06K 9/00* (2006.01)
(52) U.S. Cl. ........................................... 382/131
(58) Field of Classification Search .......... 382/128–132; 378/51, 54, 62
See application file for complete search history.

(56) References Cited

U.S. PATENT DOCUMENTS

2003/0103664 A1   6/2003   Wei et al.
2003/0147490 A1*  8/2003   Stabe et al. ............ 378/4
2005/0113664 A1   5/2005   Stefani et al.

FOREIGN PATENT DOCUMENTS

EP    1225541 A2   7/2002

* cited by examiner

*Primary Examiner* — Courtney Thomas

(57) ABSTRACT

Generating at least one view (420) of a portion of a computed tomography image includes selecting (310) a seed point (410) for a structure of interest within the image, pre-processing (320) a region of interest surrounding the seed point, estimating (325) at least one inertia axis for the region of interest, and generating (345) the at least one view from one or more of three planes that include the seed point and are orthogonal to each axis of inertia.

17 Claims, 4 Drawing Sheets

AUTOMATIC GENERATION OF OPTIMAL VIEWS FOR COMPUTED TOMOGRAPHY THORACIC DIAGNOSIS

The embodiments disclosed herein relate to providing optimized views of elongated structures for medical imaging applications.

There is a common need for generating optimized views of anatomical structures in medical practice. In particular, the generation of optimized views of elongated structures has taken on special relevance with the development of three dimensional (3D) medical imaging modalities. Exemplary applications include coronary artery single plane display and bronchial tree visualization.

Analyzing 3D data volumes is often an unfriendly, time-consuming task that requires the user to analyze vast amounts of information through necessarily partial views. Additionally, the interaction process with the data is difficult for individuals not used to handling rotations and translations in space.

Several approaches have been used to simplify interaction with 3D data, generally these approaches are very application specific. Among these, the generation of optimized views of certain anatomical structures, in particular elongated structures such as veins, bronchi, bones and such, has been successful in certain clinical practices.

The reason for this success may be that the techniques currently employed enormously simplify the task of analyzing the target structure, which might otherwise require browsing several images, displaying partial views of the target, or manually aligning the structure by manipulating the six degrees of freedom involved. These tasks generally require powerful equipment and a high degree of practical experience. The disadvantages of these methods include segmentation of the target structure to generate the view, which tends to make the methods relatively slow and not robust.

It would be advantageous to provide a single-click, non-segmentation-based automatic optimization of the display of elongated structures.

In one embodiment, a scanning system for generating at least one view of a portion of a computed tomography image includes a controller having a plurality of interconnected devices having a device for selecting a seed point for a structure of interest within the image, a device for preprocessing a region of interest surrounding the seed point, a device for estimating at least one inertia axis for the region of interest, and a device for generating the at least one view from one or more of three planes that include the seed point and are orthogonal to each axis of inertia.

A method of generating at least one view of a portion of a computed tomography image includes selecting a seed point for a structure of interest within the image, pre-processing a region of interest surrounding the seed point, estimating at least one inertia axis for the region of interest, and generating the at least one view from one or more of three planes that include the seed point and are orthogonal to each axis of inertia.

In another embodiment, a computer program product includes a computer useable medium having a computer readable program, where the computer readable program when executed on a computer causes the computer to generate at least one view of a portion of a computed tomography image by selecting a seed point for a structure of interest within the image, pre-processing a region of interest surrounding the seed point, estimating at least one inertia axis for the region of interest, and generating the at least one view from one or more of three planes that include the seed point and are orthogonal to each axis of inertia.

The foregoing aspects and other features of the present invention are explained in the following description, taken in connection with the accompanying drawings, wherein.

Figure 1A:
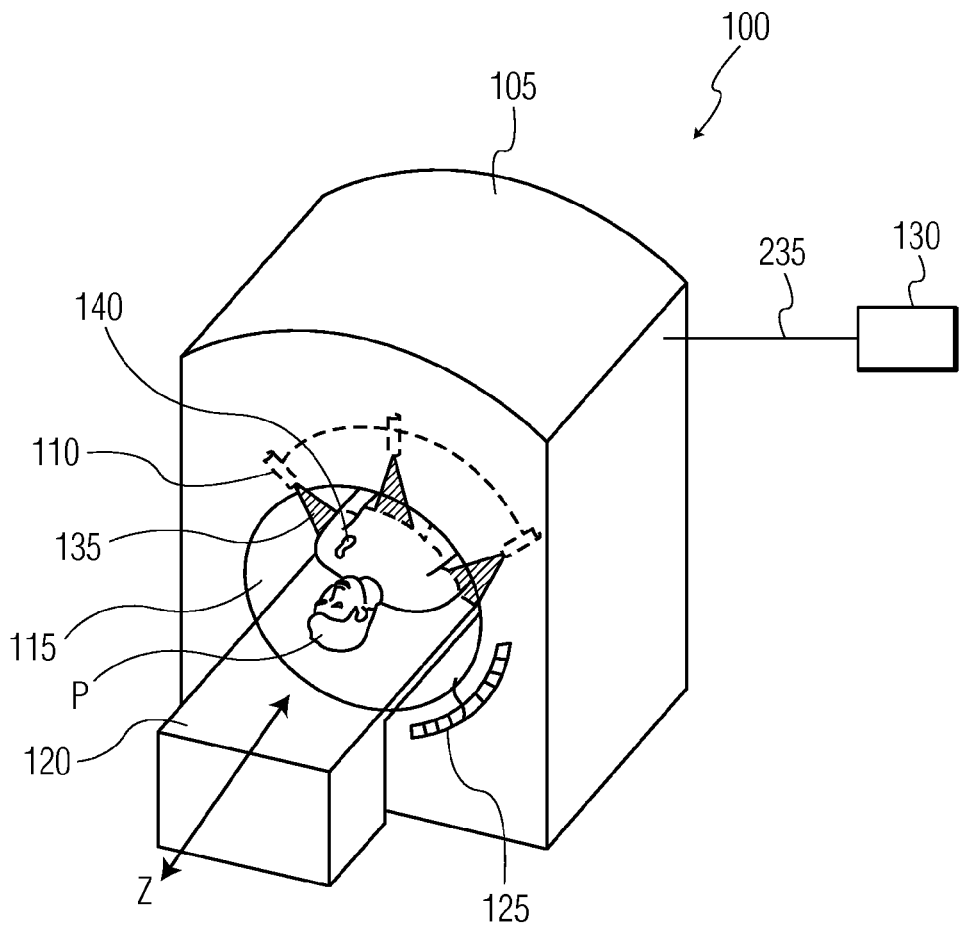
FIGS. 1A and 1B show schematic diagrams of imaging systems suitable for practicing the disclosed embodiments.

FIG. 1 shows a block diagram of a system 100 suitable for practicing the embodiments disclosed herein. Although the disclosed embodiments are described with reference to the embodiment shown in the drawings, it should be understood that the present invention can be embodied in many alternate forms of embodiments. In addition, any suitable size, shape or type of elements or materials could be used.

The present invention provides an alternative approach to those currently available in the art and is based on local orientation estimation that does not require segmentation. In addition, the techniques described herein may generate optimized views with a single user click.

The disclosed embodiments utilize image processing operations to estimate the orientation of an elongated structure around a seed point defined by the user. Once the orientation has been determined, it is used to automatically generate optimal views where the structure of interest is displayed in its full length.

By applying this method, the analysis of elongated structures in 3D CT data volumes can be performed as a single-click operation with very little delay, instead of painstakingly having to adjust up to six different parameters to find the optimal view, as is presently required.

An exemplary application for the disclosed embodiments includes computer tomography (CT) based lung diagnosis and staging. In lung studies, a clinician may slowly browse a large set of CT slides looking for different signs of illness. Those signs may include several alterations of the tree-like structure of the bronchi, which are not always easy to assess in a slice-per-slice basis. Thus, an optimized view of the bronchi would be very useful for this particular application. Existing approaches rely on the extraction of the bronchial tree for this purpose; however, this extraction requires a time-consuming pre-processing stage, and current segmentation techniques fail to extract the finer bronchioles. The techniques described herein are capable of quickly generating suitable views of the bronchial structure around a certain region of interest.

FIG. 1A shows an exemplary scanning system 100 suitable for practicing the embodiments disclosed herein. The scanning system 100 includes an imager 105, in this embodiment a computed tomography (CT) imaging scanner, which has an x-ray source 110, an examination region 115, a patient support 120, and an x-ray detector 125. The scanning system 100 also includes a controller 130 for controlling the x-ray source 110, the x-ray detector 125, and the patient support 120, and for processing data acquired by the x-ray detector 125.

Scanning system 100 may have a bore type configuration where the examination region is enclosed. The x-ray source 110 may be controlled to produce a fan-shaped, cone-shaped, wedge-shaped, or any other desirably shaped x-ray beam 135. The x-ray beam 135 may be directed through the examination region 115 and patient P toward the x-ray detector 125. The x-ray source 110 and x-ray detector 125 may be rotatable around an axis Z defined by a length of the patient support 120. The x-ray source 110 and x-ray detector 125 may be rotated together and in one embodiment may be connected by a gantry. In another embodiment the x-ray source 110 or the x-ray detector 125 may remain stationary while the other rotates such that x-rays from the x-ray source 110 impinge upon a continuously shifting angular portion of the x-ray detector 125.

The x-ray detector 125 may span a particular angular range and may include an array of detector elements for simultaneously acquiring image data. The examination region 115 generally encloses a patient P through which the x-ray beam passes. The patient P is arranged on the patient support 120 which may be linearly movable along the Z axis.

Figure 1B:
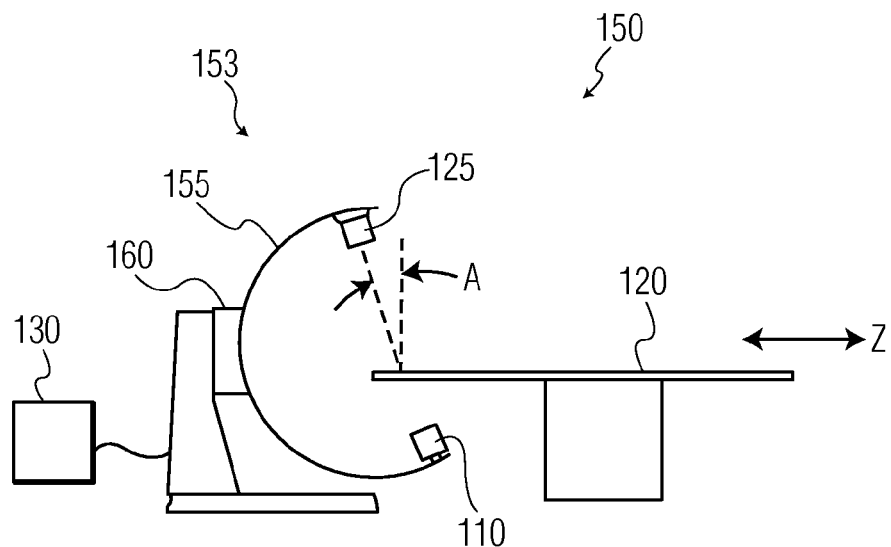

FIG. 1B shows an alternate exemplary scanning system 150 with an imager 153 having open C-arm configuration. Similar to imager 105, imager 153 includes x-ray source 110, examination region 115, patient support 120, and x-ray detector 125. Scanning system 150 includes controller 130 for controlling the x-ray source 110, the x-ray detector 125, and the patient support 120, and for processing data acquired by the x-ray detector 125. Scanning system 150 utilizes a c-arm structure 155 to connect and support the x-ray source 110 and x-ray detector 125. A yoke 160 allows the controller 130 to adjust the x-ray source 110 and x-ray detector 125 in an angular direction A around an axis perpendicular to the Z axis. In this configuration, the x-ray source 110 and x-ray detector 125 are generally rotated together.

Figure 2:
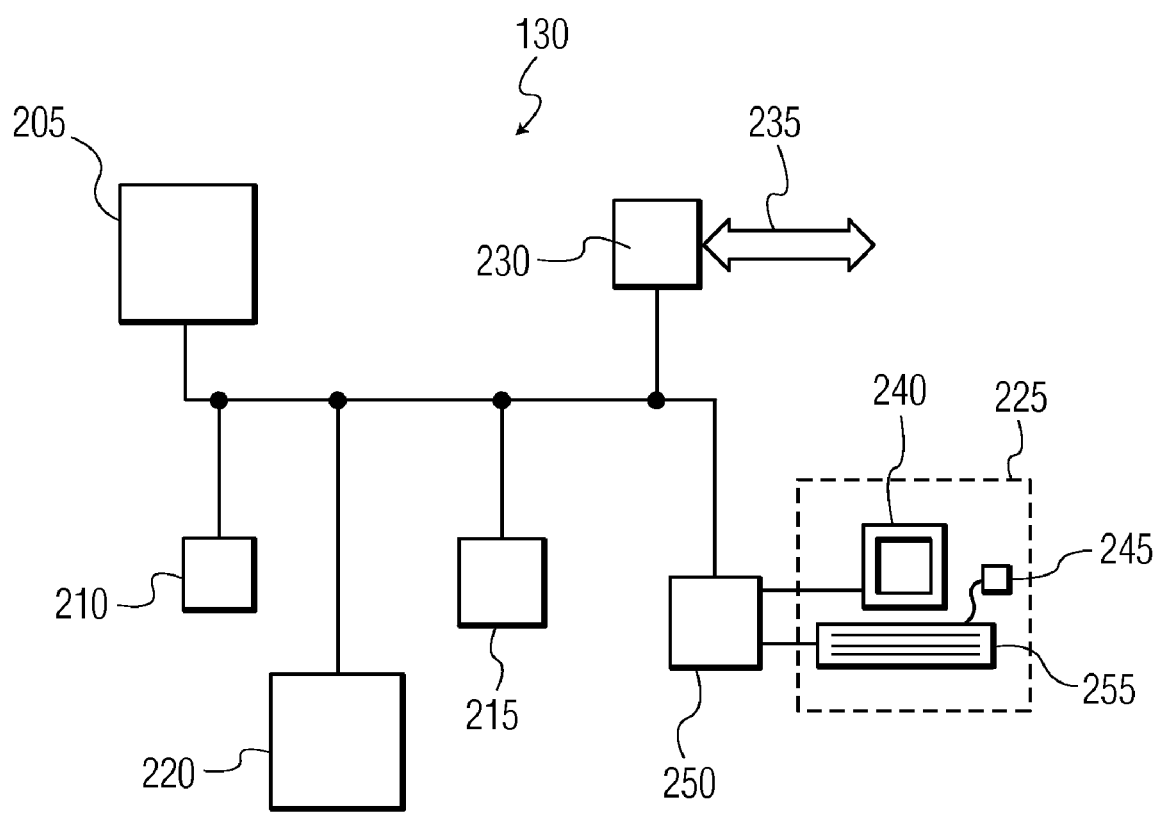
FIG. 2 illustrates an exemplary controller for operating the imaging systems.

FIG. 2 shows a block diagram of the controller 130. The controller generally includes circuitry implementing a processor 205, read only memory 210, random access memory 215, program storage 220, a user interface 225, and a network interface 230.

Processor 205 is generally operable to read information and programs from a computer program product, for example, a computer useable medium, such as read only memory 210, random access memory 215, or program storage 220.

Both read only memory 210 and random access memory 215 may utilize semiconductor technology or any other appropriate materials and techniques. Program storage 220 may include a computer usable medium, for example, a diskette, a computer hard drive, a compact disk, a digital versatile disk, an optical disk, a chip, a semiconductor, or any other device capable of storing programs in the form of computer readable code.

Read only memory 210, random access memory 215, and program storage 220, either individually or in any combination comprise a computer program product including a computer useable medium having a computer readable program, wherein the computer readable program when executed by the controller 130, causes the controller 130 to control the x-ray source 110, x-ray detector 125, and the patient support 120, and to process data acquired by the imagers 105, 153 to automatically generate views for CT thoracic diagnosis according to the techniques described herein.

The network interface 230 may be generally adapted to provide an interface between the controller 130 and the components of the imager 105 through a communication network 235. Communication network 235 may be any suitable communication path including the Public Switched Telephone Network (PSTN), the Internet, a wireless network, a wired network, a Local Area Network (LAN), a Wide Area Network (WAN), a virtual private network (VPN) etc., and may further include other types of networks including X.25, TCP/IP, ATM, etc. In one embodiment, communication network 120 may be an IEEE 1349 network, also referred to as a "Firewire" network.

The controller 130 may include a user interface 225 with a display 240 and an input device 255 such as a keyboard and a pointing device 245 such as a mouse. The user interface may be operated by a user interface controller 250 under control of processor 205.

Returning to FIGS. 1A and 1B, in a helical imaging mode, the x-ray source 110 and x-ray detector 125 may rotate simultaneously with a linear advancement of the patient support 120 to produce a generally helical trajectory of the x-ray source 110 about the patient support 120.

In a multi-slice imaging mode, the x-ray source 110 and x-ray detector 125 may rotate while the patient support 120 remains stationary to produce a generally circular trajectory of the x-ray source 110 about the patient support 120 while an axial slice image of the patient P is acquired by the controller 130. This process may be repeated in an iterative fashion as the patient support 120 is advanced along the Z axis to acquire imaging data in discrete steps along the Z axis.

Thus, the controller 130 may control the x-ray source 110, x-ray detector 125, and the patient support 120 to obtain selected projection views of the patient P along a helical or circular trajectory of the x-ray source 110 about the patient support 120. The projection views may be collected at a variable frame rate determined by the controller 130. The controller 130 collects the projection views for processing and for adjustment of the data acquisition process according to the disclosed embodiments.

The trajectory of the x-ray source 110 during acquisition of the projection views preferably provides substantial angular coverage for each volume pixel, or voxel, of the imaged region of interest to reduce image artifacts. Projection data collected by the x-ray detector 125 is communicated to the read only memory 210, random access memory 215, or program storage 220, either individually or in any combination for further processing.

Figure 3:
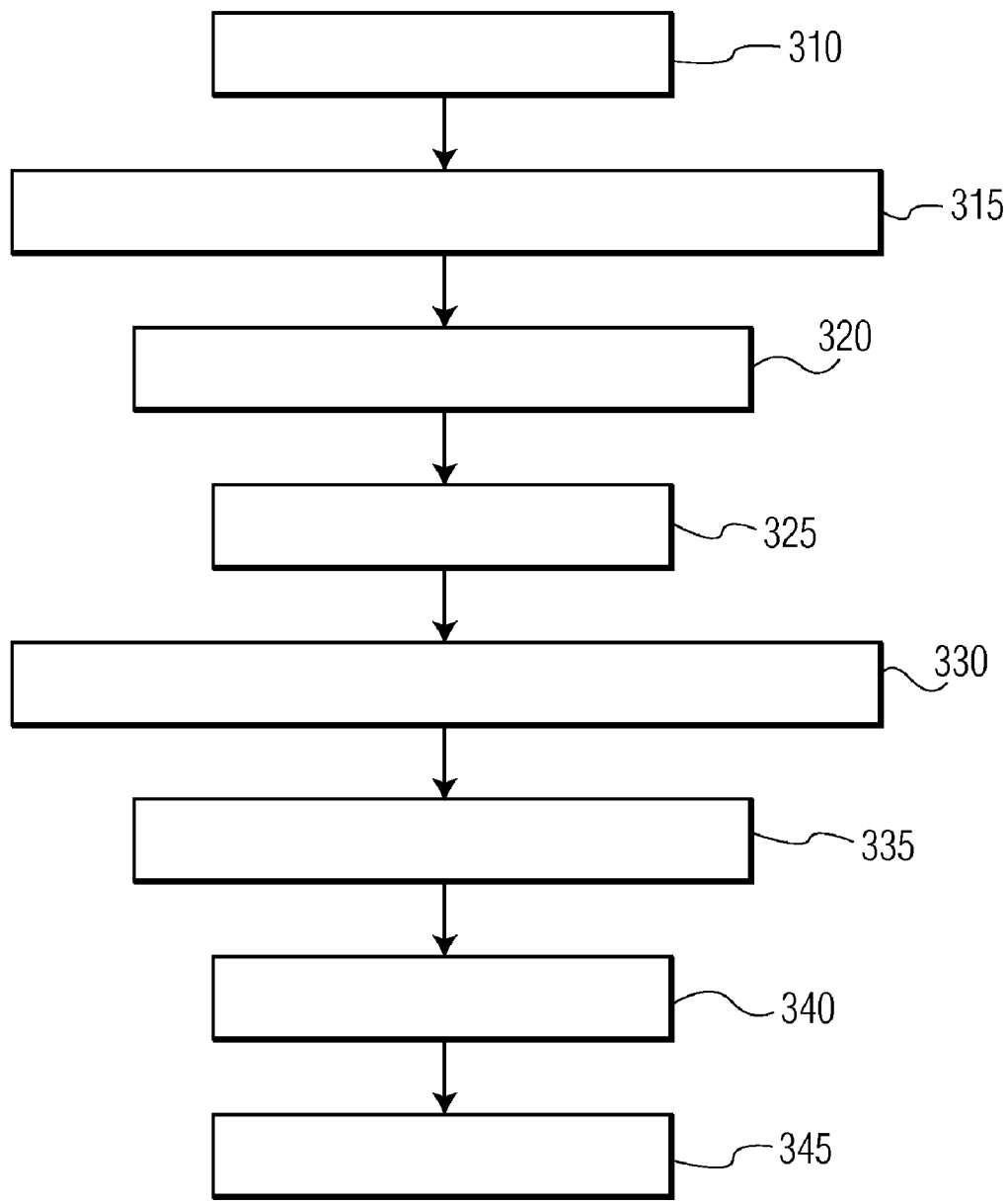
FIG. 3 shows a flow diagram of a procedure for automatic generation of optimized views of elongated structures.

FIG. 3 shows an exemplary procedure for generating views according to the invention. The procedure may be implemented as a computer readable program incorporated in a computer usable medium as described above. The procedure may be implemented as a number of devices, including hardware, software, or a combination of both, each designed to carry out the functions described in each block. In one embodiment, the devices may be incorporated within the controller 130.

A user generally initiates data acquisition, typically by interacting with user interface 225 (FIG. 2). The user operates the scanning system 100, 150 to acquire a series of images utilizing, for example, a multi-slice or helical imaging mode as described above.

The data from all the slices acquired by the imagers 105, 153 represents a data volume that may be processed by the controller 130 to generate images and to perform analyses. The controller 130 operates to display the images on display 240 for viewing by the user. The user generally reviews the images and selects those for further examination.

Referring to again to FIG. 3, the central components of the procedure are: selecting a seed point for a structure of interest within the image 310, pre-processing a region of interest surrounding the seed point 320, estimating at least one inertia axis for the region of interest 325, and generating at least one view from one or more of three planes that include the seed point and are orthogonal to each axis of inertia 345.

Figure 4:
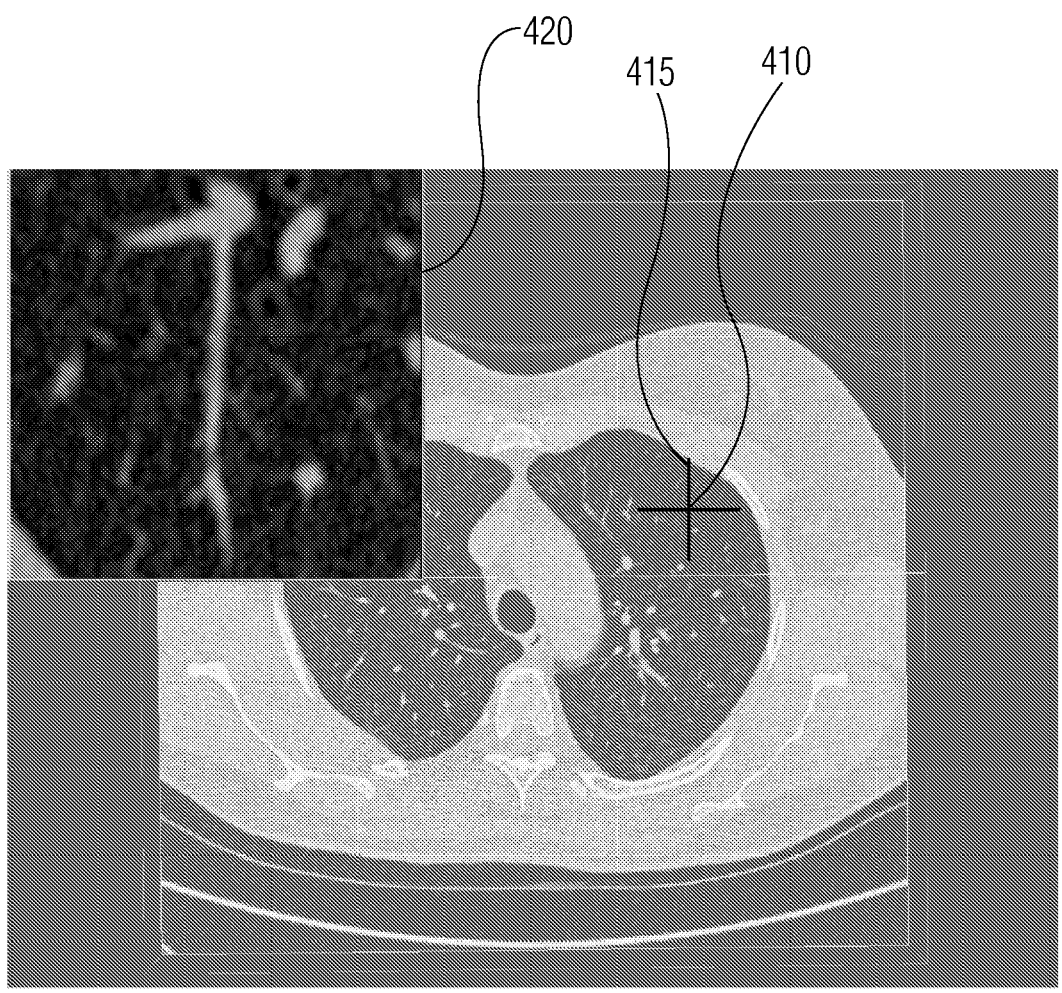
FIG. 4 shows an initial image and an exemplary optimized view of a selected portion of the image.

Referring again to FIG. 3 in greater detail, in block 310, the user determines a seed point for a structure of interest present in an image on display 240. An exemplary displayed image is shown in FIG. 4. The seed point 410 may be indicated by crosshairs 415 activated and positioned by the user using the input device 255 or pointing device 245. According to the disclosed embodiments, the user may then operate the pointing device 245 to "click" or otherwise select or indicate the seed point and activate the generation of one or more optimal views. The seed point may also be selected or indicated by the user operating the input device 255.

In other embodiments, the seed point selection may be semi-automatic or automatic. For example, a program may choose a portion of an image for further investigation by a user, where the user then selects a seed point. Alternately, the program may select the seed point itself, without any guidance by the user, and then may proceed to generate one or more optimized views of the associated structure.

In block 315 the procedure automatically performs a local search around the user determined seed point 410 to refine the location of the seed point. The user determined seed point 410 may not be the best choice for optimal view generation. Thus, the local search involves analyzing the voxels proximate the seed point within the structure of interest to refine the location of the seed point. The analysis may include criteria different that those used by the user. Exemplary criteria for the local search may include identifying a local maximum, minimum, or both, which may be centered with respect to the structure of interest.

In block 320, a preprocessing technique may optionally be performed on a region of interest centered on the seed point to improve robustness against noise, artifacts and nearby structures. In one embodiment, the region of interest may be first defined as including the voxels surrounding the seed point and extending to the boundaries of the structure of interest. An auto-correlation transformation may then be performed on the defined region of interest. Generally, the auto-correlation transformation may measure the average magnitude of the correlation of a voxel over time to yield an expectation value. The expectation values depend on how quickly the data changes over time and may be used to filter out noise and artifacts. Alternately, other preprocessing techniques may be used, for example, low pass filtering, anisotropic smoothing, etc.

As shown in block 325, in one embodiment, density values are assigned to every voxel in the region of interest depending on each voxel's intensity and distance to the seed point. Based on the assigned density values, a main axis of inertia and two other axes of inertia, orthogonal to the main axis, are estimated for the region of interest. Other techniques may also be utilized to estimate the axes of inertia, for example, linear and non linear filtering, Gaussian intensity modeling, etc.

Referring to block 330, in some instances, the axis estimation obtained in block 325 may optionally require further refinement. One refinement technique may include generating a series of 2 dimensional (2D) orthogonal slices along the main inertia axis. In block 335, the crossing point for each 2D slice may be refined. The crossing point is defined as the center point of the structure of interest within the particular slice. In the refinement process, the intersection of the particular slice with the main inertia axis may be used as an initial estimate. A simple gradient descent technique may then be used in each slice to locate the center point of the structure of interest within each slice. This may then be utilized as a new crossing point for the slice.

In block 340, a new main inertia axis may be computed. For the technique that includes generating a series of 2D orthogonal slices along the main inertia axis described above, the main inertia axis may be computed by fitting a line to the set of all the crossing points for all the slices. Other techniques may also be utilized to generate a new main inertia axis if required, including fitting a curved plane to the points defining the axis of inertia. Once the new main inertia axis is determined, the other two inertia axes are rotated accordingly to maintain their orthogonality with the new main inertia axis. In block 345, up to three new optimized views of the structure of interest can be generated utilizing one or more of three planes that include the seed point and are orthogonal to each axis of inertia.

Inset 420 of FIG. 4 shows one exemplary view resulting from the procedure of FIG. 3. It should be noted that the procedure of FIG. 3 may be implemented such that when the user determines the seed point in block 310 of FIG. 3 and clicks or otherwise selects or indicates the seed point, the optimal view or views are then displayed with little or no delay perceptible by the user.

While the embodiments above are discussed as an implementation within the controller 130, it should be understood that the procedure and devices may also be implemented in a stand alone workstation, for example a desktop or portable computer remote from the imaging system 100, 150. As long as the data volume described above is provided to the procedure, the procedure may operate in the controller 130, a stand alone workstation or may be distributed among a number of computing devices suitable for performing the techniques described herein.

While discussed in the context of examining bronchial structures, it should be noted that the disclosed embodiments are applicable to any medical imaging application where elongated structures are present. Another exemplary application may include generating optimal views of coronary arteries in CT scans.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

The invention claimed is:

1. A scanning system for generating at least one view of a portion of a computed tomography image comprising:
   a controller having a plurality of interconnected devices including:
      a device for selecting a seed point for a structure of interest within the image;
      a device for preprocessing a region of interest surrounding the seed point;
      a device for estimating at least one inertia axis for the region of interest, wherein the device for estimating at least one inertia axis:
         assigns density values to voxels in the region of interest depending on each voxel's intensity and distance to the seed point; and
         utilizes the density values to define a main axis of inertia and two other axes of inertia orthogonal to the main axis of inertia; and
      a device for generating the at least one view from one or more of three planes, defined by one or more of the three axes, that include the seed point and are orthogonal to the at least one axis of inertia.

2. The system of claim 1, wherein the device for selecting a seed point performs a local search to refine the seed point.

3. The system of claim 2, wherein the local search includes analyzing voxels proximate the seed point within the structure of interest by identifying a local maximum or minimum centered within the structure of interest.

4. The system of claim 1, wherein the device for preprocessing a region of interest auto-correlates the region of interest.

5. The system of claim 1, wherein the device for preprocessing a region of interest defines the region of interest as voxels surrounding the seed point and extending to boundaries of the structure of interest.

6. The system of claim 1, wherein the device for estimating at least one inertia axis further defines the main axis of inertia by: generating a plurality of 2 dimensional orthogonal slices along the main inertial axis; locating a center point of the structure of interest within each slice; and fitting a line to the center points of interest for the plurality of slices.

7. A method of generating at least one view of a portion of a computed tomography image comprising:
　selecting seed point for a structure of interest within the image;
　pre-processing a region of interest surrounding the seed point;
　estimating at least one inertia axis for the region of interest, wherein estimating at least one inertia axis includes:
　　assigning density values to voxels in the region of interest depending on each voxel's intensity and distance to the seed point; and
　　utilizing the density values to define a main axis of inertia and two other axes of inertia orthogonal to the main axis of inertia; and
　generating the at least one view from one or more of three planes that include the seed point and are orthogonal to each axis of inertia.

8. The method of claim 7, wherein selecting a seed point includes performing a local search to refine the seed point.

9. The method of claim 8, wherein the local search includes analyzing voxels proximate the seed point within the structure of interest by identifying a local maximum or minimum centered within the structure of interest.

10. The method of claim 7, wherein pre-processing a region of interest includes auto-correlating the region of interest.

11. The method of claim 7, wherein pre-processing a region of interest includes defining the region of interest as voxels surrounding the seed point and extending to boundaries of the structure of interest.

12. The method of claim 7, wherein the main axis of inertia is further defined by: generating a plurality of 2 dimensional orthogonal slices along the main inertial axis; locating a center point of the structure of interest within each slice; and fitting a line to the center points of interest for the plurality of slices.

13. A computer program product comprising a computer useable medium having a computer readable program, wherein the computer readable program when executed on a computer causes the computer to generate at least one view of a portion of a computed tomography image by:
　selecting seed point for a structure of interest within the image; pre-processing region of interest surrounding the seed point;
　estimating at least one inertia axis for the region of interest, wherein estimating at least one inertia axis includes:
　　assigning density values to voxels in the region of interest depending on each voxel's intensity and distance to the seed point; and
　　utilizing the density values to define a main axis of inertia and two other axes of inertia orthogonal to the main axis of inertia; and
　generating the at least one view from one or more of three planes that include the seed point and are orthogonal to each axis of inertia.

14. The computer program product of claim 13, wherein selecting a seed point includes performing a local search to refine the seed point.

15. The computer program product of claim 14, wherein the local search includes analyzing voxels proximate the seed point within the structure of interest by identifying a local maximum or minimum centered within the structure of interest.

16. The computer program product of claim 13, wherein auto-correlating a region of interest includes defining the region of interest as voxels surrounding the seed point and extending to boundaries of the structure of interest.

17. The computer program product of claim 13, wherein the main axis of inertia is further defined by: generating a plurality of 2 dimensional orthogonal slices along the main inertial axis; locating a center point of the structure of interest within each slice; and fitting a line to the center points of interest for the plurality of slices.

* * * * *